(12) United States Patent
Lieberman et al.

(10) Patent No.: US 6,221,028 B1
(45) Date of Patent: Apr. 24, 2001

(54) VITRECTOMY LENS WITH INTEGRATED ILLUMINATOR

(75) Inventors: Robert A. Lieberman, Torrance; Edgar A. Mendoza, Redondo Beach, both of CA (US)

(73) Assignee: Intelligent Optical Systems, Inc., Torrance, CA (US)

( * ) Notice: Subject to any disclaimer, the term of this patent is extended or adjusted under 35 U.S.C. 154(b) by 0 days.

(21) Appl. No.: 09/348,366

(22) Filed: Jul. 7, 1999

(51) Int. Cl.$^7$ .................................................. A61B 5/00
(52) U.S. Cl. ............................ 600/558; 351/200; 606/4
(58) Field of Search ........................... 600/558; 351/212, 351/216, 221

(56) References Cited

U.S. PATENT DOCUMENTS

| | | | |
|---|---|---|---|
| 3,780,979 | * 12/1973 | de Guillebon | 351/16 |
| 5,133,708 | * 7/1992 | Smith | 606/5 |
| 5,521,657 | * 5/1996 | Klopotek | 351/212 |
| 5,608,972 | * 3/1997 | Szirth et al. | 351/206 |

* cited by examiner

Primary Examiner—Cary O'Connor
Assistant Examiner—Pamela L. Wingwood
(74) Attorney, Agent, or Firm—Herbert M. Shapiro

(57) ABSTRACT

The inner eye of a surgical patient is illuminated by incorporating an optical fiber in a ring configuration imbedded into or attached to a contact lens. The viewing surface of the lens if planar to optimize the surgeon's view. The opposite surface of the lens is curved to conform to the patient's eye. A solution conduit irrigates the eye. The apparatus is easily positioned and easily directed. The apparatus also is sufficiently inexpensive to be disposable.

8 Claims, 2 Drawing Sheets

VITRECTOMY LENS WITH INTEGRATED ILLUMINATOR

REFERENCE TO RELATED APPLICATIONS

The present application is a Continuation-in-Part of patent application Ser. No. 09/334,845 filed Jun. 16, 1999 for R. Lieberman and C. Egalon and assigned to the assignee of the present application. This application is incorporated herein by reference.

FIELD OF THE INVENTION

This invention relates to apparatus for illuminating the inner eye of a patient during surgery.

BACKGROUND OF THE INVENTION

Optical fibers or channel waveguides are well known and commercially available. The use of such components as sensors for physical or chemical phenomenon is described in U.S. Pat. No. 4,321,057 issued Mar. 23, 1982 to Richard G. Buckles.

The above-noted copending application describes techniques for controlling the power dissipated per unit length of an optical fiber in order to, for example, provide a linear sensitivity over the length of a fiber. The application also describes such techniques for optical fibers and resulting uniform power dissipation for uniform illumination purposes.

Present eye illumination apparatus is bulky, costly, and cumbersome and produces light which is difficult to direct precisely to the area a surgeon wishes to illuminate.

BRIEF DESCRIPTION OF THE INVENTION

In accordance with the principles of this invention, an optical fiber (or channel waveguide) configured to provide uniform illumination, in response to white light launched therein, in one embodiment of the fiber is attached to a corneal contact lens to provide a ring illuminator thereabout. In another embodiment, the fiber is embedded, as a ring illuminator, within the body of the contact lens. In a further embodiment, a plurality of optical fibers is used with fiber ends arranged around the periphery of a contact lens. A mirror is positioned at each fiber end to direct light to illuminate the entire inner eye and prevent shadows.

The contact lens is not necessarily contoured to correct the vision of the patient. Instead, the lens has a contoured surface to follow the contour of the eye of the patient and a planar outer surface which serves as the surgeon's viewing surface.

DETAILED DESCRIPTION OF ILLUSTRATIVE EMBODIMENTS OF THE INVENTION

Figure 1:
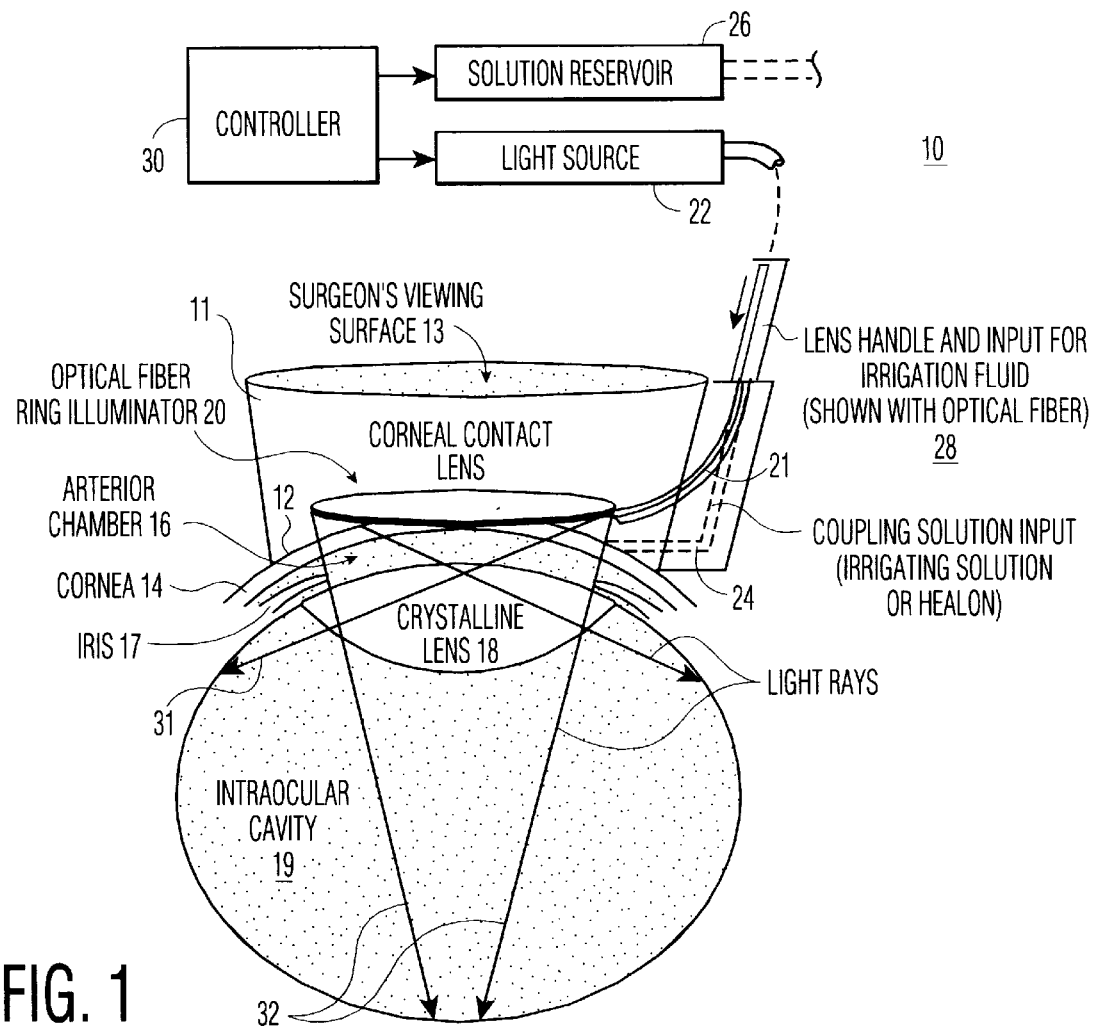
FIG. 1 is a schematic side view of apparatus in accordance with the principles of this invention positioned with respect to an eye of a patient.

FIG. 1 shows apparatus 10 in accordance with one embodiment of this invention. The apparatus comprises a corneal contact lens 11 with a curved lower surface 12 and a planar top surface 13. The lower surface is shown juxtaposed with the cornea 14 of the eye of a patient. The anterior chamber 16, the iris 17, the crystalline lens 18 and the intraocular cavity 19 of the eye also are shown.

In accordance with the principles of the invention, lens 11 includes an optical fiber ring illuminator 20. The optical fiber extends from the ring at 21 to form a light path (pigtail) from a source 22 of white light. The lens also includes a solution conduit 24 for introducing a solution between the lens and the cornea. Conduit 24 is connected to a reservoir 26. The fiber optic pigtail (21) and the solution conduit (24) are shown contained in a handle 28 attached to lens 11. The solution is index matched to avoid back reflection of the light from the ring illuminator. A controller 30 for activating light source 22 and for pumping the solution conveniently resides in the handle for use by a medical practitioner.

The illumination of the interior of the eye is indicated by arrows 31 and 32. The handle may be adapted to connect to a disposable lens which houses a ring illuminator and a solution conduit by providing for suitable connectors (not shown). Alternatively, the ring illuminator may be fabricated as a permanent part of the handle. In such an embodiment, a corneal contact lens is conveniently snap-fit into the space defined by the ring illuminator and disposed of after use.

Figure 2:
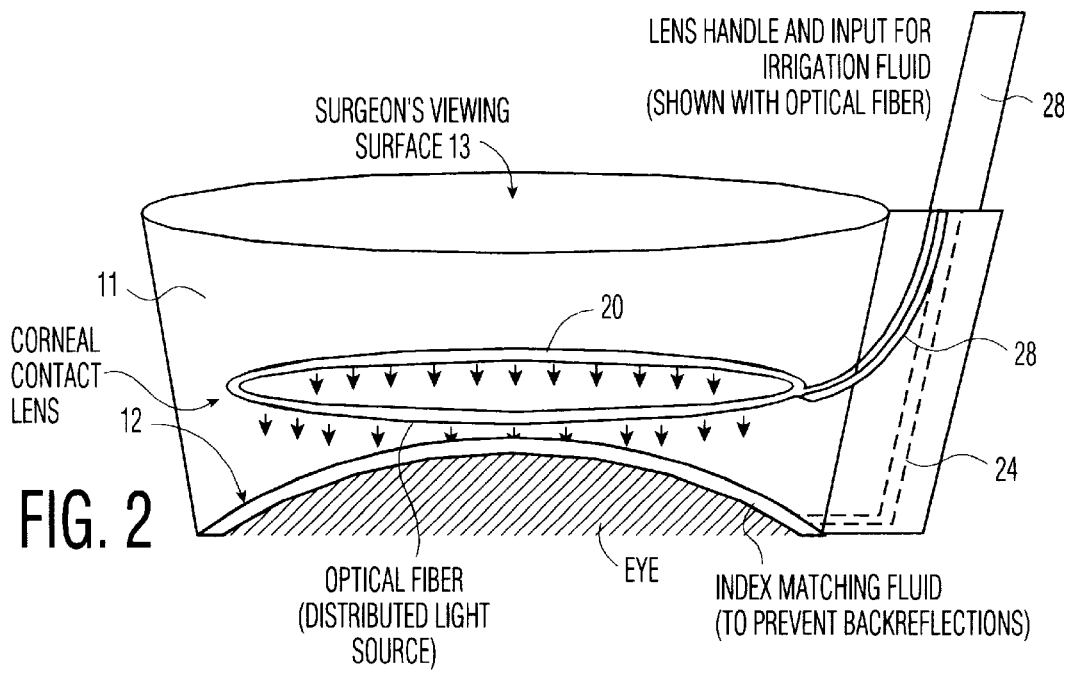
FIGS. 2 and 3 are schematic side and top views, respectively of a position of the apparatus of FIG. 1.
Figure 3:
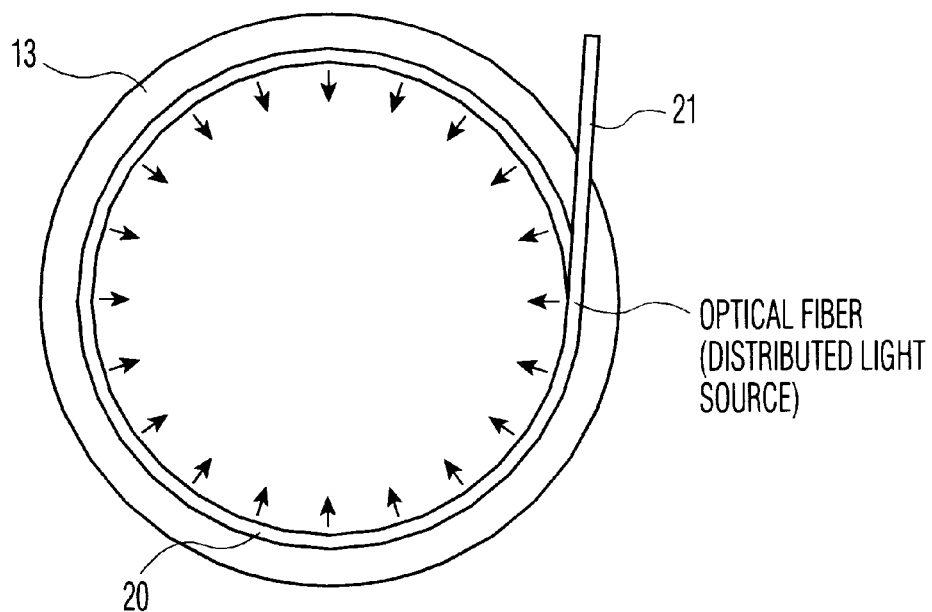
Figure 4:
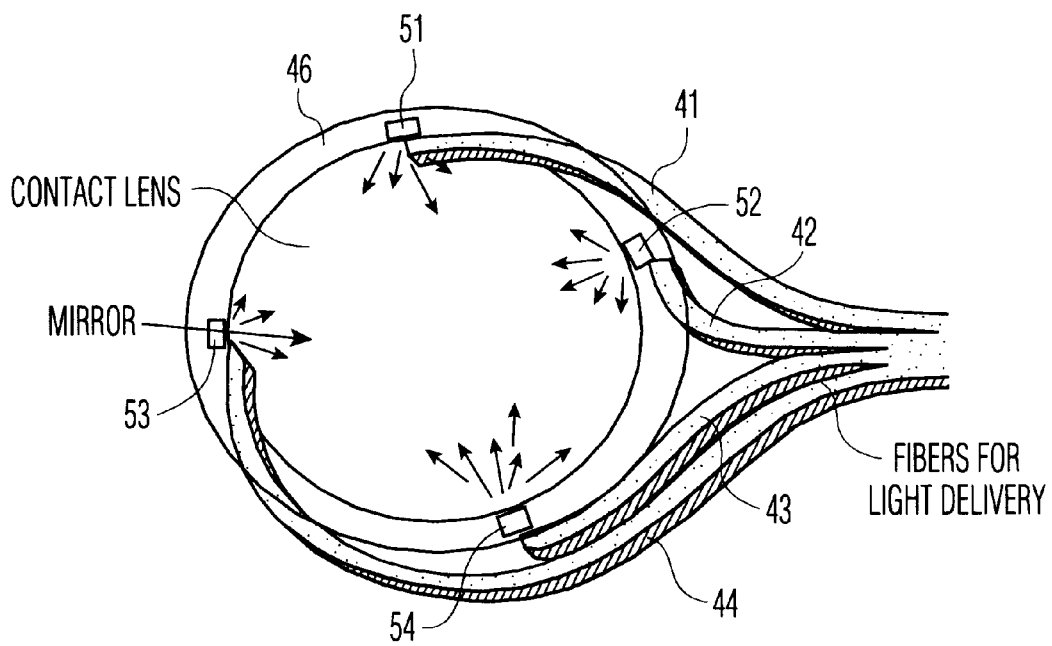
FIG. 4 is a schematic top view of an alternative apparatus in accordance with the principles of this invention.

FIGS. 2 and 3 are side and top views, respectively, with the ring illuminator 20 shown directing light downwards as viewed in FIG. 2 and inward as viewed in FIG. 3. The direction of illumination is represented by the downward directed arrows in FIG. 2 and the inward directed arrows in FIG. 3. The illumination around the ring is represented to be uniform and is achieved by modifying a physical property of the fiber by any one of a variety of techniques described in the above-noted patent application by:

a) Increasing the core/cladding refractive index ratio along the fiber length;
b) Increasing the core diameter along the fiber length;
c) Increasing the absorption coefficient of the cladding along the fiber length;
d) Increasing the scattering coefficient of the fiber core along the fiber length; and
e) Varying the parameters (a, b, & c) together or in varying combinations;

FIG. 4 shows a schematic top view of an alternative embodiment of this invention. The embodiment of FIG. 4 is similar to that of FIGS. 1–3 except that a plurality of optical fibers 41, 42, 43, and 44 is shown with the ends of the fibers terminating within a corneal contact lens (like 11 of FIGS. 1–3) around an imaginary circle 46. The ends of the fibers are polished and each of the fibers directs light towards an associated mirror 51, 52, 53 and 54 respectively. The mirrors direct light in the desired direction as indicated by the arrows in FIGS. 2 and 3. Alternatively, a scattering site is provided at the end of each fiber around circle 46 serving to direct light as indicated by the arrows of FIGS. 2 and 3.

The invention has been described in terms of optical fibers. The invention may be implemented with any convenient means for defining an optical path such as a channel waveguide as should be apparent to one skilled in the art. The invention also is suitable for illuminating the field of view through a microscope.

What is claimed is:

1. Apparatus including a corneal contact lens having a curved first surface and defining a field of view, said apparatus including means for illuminating said field of view, said means including an optical fiber, said fiber being structured by modifying a physical property of said fiber to emit light uniformly therealong and being contoured to direct light launched therein towards said first surface in a manner to illuminate said field of view uniform.

2. Apparatus as in claim 1 wherein said fiber is contoured into a ring configuration.

3. Apparatus including a corneal contact lens having a curved first surface and defining a field of view, said apparatus including means for illuminating said field of view, said means comprising an optical fiber contoured to direct light launched therein towards said first surface in a manner to illuminate said field of view uniformly, said fiber being embedded in said lens.

4. Apparatus as in claim 3 also including a source of white light coupled to an input end of said fiber.

5. Apparatus as in claim 4 also including a source of irrigation solution and means coupled to said lens for delivering said solution to the space between said first surface and a patient's eye.

6. Apparatus as in claim 5 wherein said lens has a second surface opposite said first surface, said second surface being planar to optimize the view of a medical practitioner.

7. Apparatus including a corneal contact lens having a curved first surface and defining a field of view, said apparatus including first means for illuminating said field of view, said first means including a plurality of optical fibers contoured to direct light launched therein towards said first surface in a manner to illuminate said field of view uniformly, said fibers having first ends arranged about an imaginary circle, said apparatus including a plurality of second means, each of said second means being positioned to direct light from an associated one of said first ends inwardly towards the axis of said circle, wherein each of said second means comprises a mirror.

8. Apparatus including a corneal contact lens having a curved first surface and defining a field of view, said apparatus including first means for illuminating said field of view, said first means including a plurality of optical fibers contoured to direct light launched therein towards said first surface in a manner to illuminate said field of view uniformly, said fibers having first ends arranged about an imaginary circle, said apparatus including a plurality of second means, each of said second means being positioned to direct light from an associated one of said first ends inwardly towards the axis of said circle, wherein each of said second means is a light-scattering site.

* * * * *